United States Patent [19]

Yano et al.

[11] Patent Number: 5,019,595

[45] Date of Patent: May 28, 1991

[54] NOVEL CARBOXYLIC ACID ESTERS AND INSECTICIDES CONTAINING THEM AS AN ACTIVE INGREDIENT

[75] Inventors: Toshihiko Yano; Yoko Torisu, both of Ashiya; Hiroko Sekihachi, Toyonaka; Noritada Matsuo, Itami; Tohei Takagaki, Nishinomiya; Kazunori Tsushima, Sapporo, all of Japan

[73] Assignee: Sumitomo Chemical Company, Ltd., Osaka, Japan

[21] Appl. No.: 585,627

[22] Filed: Sep. 20, 1990

Related U.S. Application Data

[63] Continuation-in-part of Ser. No. 360,487, Jun. 2, 1989, abandoned.

[30] Foreign Application Priority Data

Jun. 10, 1988 [JP] Japan ................ 63-144143

[51] Int. Cl.$^5$ ............................. A01N 53/00
[52] U.S. Cl. ...................... 514/531; 560/124
[58] Field of Search ................... 560/124; 514/531

[56] References Cited

U.S. PATENT DOCUMENTS

| 3,876,681 | 4/1975 | Okuno | 560/124 |
|---|---|---|---|
| 3,934,023 | 1/1976 | Okuno et al. | 424/274 |
| 4,024,163 | 5/1977 | Elliott | 560/124 |
| 4,489,093 | 12/1984 | Martel | 560/124 |
| 4,496,586 | 1/1985 | Matsui | 560/124 |
| 4,883,806 | 11/1989 | Martel | 560/124 |

FOREIGN PATENT DOCUMENTS

| 0041021 | 12/1981 | European Pat. Off. . |
|---|---|---|
| 0050534 | 4/1982 | European Pat. Off. . |
| 2201036 | 4/1974 | France . |
| 52-45768 | 11/1977 | Japan . |
| 57-126447 | 8/1982 | Japan . |
| 2055822 | 3/1981 | United Kingdom . |

OTHER PUBLICATIONS

Chemical Abstracts, Tenth Collective Index, vol. 86-95, 1977-1981, Chemical Substances, pp. 17611CS and 17612CS.

Chemical Abstracts, vol. 88, No. 19, May 8, 1978, p. 143, Abstract No. 132035s.

Elliott, Chem. Soc. Rev., vol. 7, pp., 473-505 (1978).

*Primary Examiner*—Michael L. Shippen
*Attorney, Agent, or Firm*—Stevens, Davis, Miller & Mosher

[57] ABSTRACT

This invention relates to a novel carboxylic acid esters represented by the formula (I) below and insecticides containing them as an active ingredient,

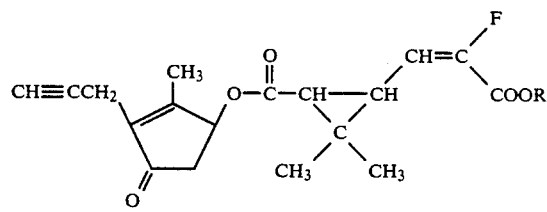

wherein R represents a $C_{1-5}$ alkyl group, a $C_{3-6}$ cycloalkyl group, a $C_{3-6}$ alkenyl group, a $C_{3-6}$ alkynyl group or a $C_{1-5}$ haloalkyl group.

14 Claims, No Drawings

NOVEL CARBOXYLIC ACID ESTERS AND INSECTICIDES CONTAINING THEM AS AN ACTIVE INGREDIENT

CROSS-REFERENCE TO RELATED APPLICATIONS

This is a continuation-in-part of application Ser. No. 07/360,487, filed on June 2, 1989, now abandoned.

The present invention relates to a novel carboxylic acid ester and insecticides containing it as an active ingredient.

Hitherto, the ester compounds, for example, described in U.S. Pat. Nos. 4,489,093, 3,934,023, 3,876,681 and JP-B-52-45758 are known to have an insecticidal activity.

However, the insecticidal effect of the compounds is not always said to be satisfactory. In view of the situation like this, the present inventors have extensively studied to develop a compound having excellent insecticidal activity, and as a result, have found that an ester compound represented by the formula (I) (hereinafter referred to as present compound) has a very high insecticidal activity:

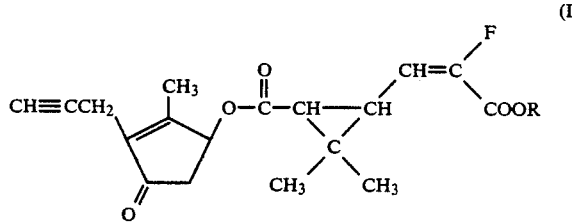

wherein R represents a $C_{1-5}$ alkyl group, a $C_{3-6}$ cycloalkyl group, a $C_{3-6}$ alkenyl group, a $C_{3-6}$ alkynyl group or a $C_{1-5}$ haloalkyl group.

The present inventors have thus completed the present invention.

The present compounds have excellent properties as follows:

(1) Act on various insect pests very rapidly and also with a high insecticidal activity.

(2) Have a high insecticidal effect especially in the form of an oil spray or aerosol.

(3) Have a high activity as a fumigant or smoking formulation.

(4) Exhibit an excellent effect on insect pests resistant to organophosphorus or carbamate insecticides.

Among the present compounds, preferred ones are those in which R is a $C_{1-4}$ alkyl group, a cyclopropyl group, a $C_{3-4}$ alkenyl group, a $C_{3-4}$ alkynyl group or a $C_{1-4}$ haloalkyl group. Particularly, those in which R is a methyl group, an ethyl group, a n-propyl group, an isopropyl group, a tert-butyl group, a cyclopropyl group, an allyl group, a propargyl group, a 2-chloroethyl group or a 2-fluoroethyl group are further more preferred, and those in which R is a methyl group, an ethyl group, an isopropyl group or a tert-butyl group are most preferred.

Referring to typical compounds of the preferred compounds, there are mentioned for example (S)-2-methyl-4-oxo-3-propargylcyclopent-2-enyl (1R)-cis-2,2-dimethyl-3-[(E)-2-ethoxycarbonyl-2-fluorovinyl]cyclopropanecarboxylate, (S)-2-methyl-4-oxo-3-propargylcyclopent-2-enyl (1R)-cis-2,2-dimethyl-3-[(E)-2-fluoro-2-methoxycarbonylvinyl]cyclopropanecarboxylate, (S)-2-methyl-4-oxo-3-propargylcyclopent-2-enyl (1R)-cis-2,2-dimethyl-3-[(E)-2-fluoro-2-isopropoxycarbonylvinyl]cyclopropanecarboxylate, (S)-2-methyl-4-oxo-3-propargylcyclopent-2-enyl (1R)-cis-2,2-dimethyl-3-[(E)-2-tert-butoxycarbonyl-2-fluorovinyl]cyclopropanecarboxylate.

The present compounds can be produced by reacting a 2-methyl-4-oxo-3-propargylcyclopent-2-en-1-ol represented by the formula (II),

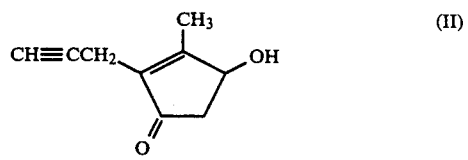

with a carboxylic acid represented by the formula (III),

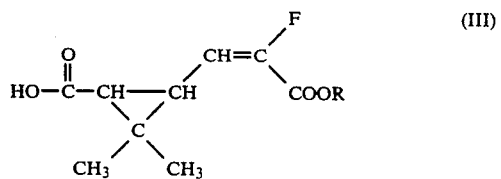

wherein R represent the same meanings as described above, or its reactive derivative, if necessary, in the presence of a suitable inert solvent, reaction auxiliary reagent or catalyst.

The reactive derivative of the carboxylic acid referred to herein includes acid halides such as acid chloride, acid bromide, etc., acid anhydrides, and the like.

The compounds of the present invention represented by the formula (I) have optical isomers due to the asymmetric carbon atoms on the acid moiety and the alcohol moiety and stereoisomers due to the acid moiety, and all of these isomers are within the scope of the present invention.

In the compounds of the present invention, the optical isomers wherein the acid moiety has an absolute configuration of (1R) and/or the alcohol moiety has an absolute configuration of (S) have very high insecticidal activities.

The method of the present invention will be illustrated with reference to a method using a carboxylic acid halide.

The present compounds are produced by reacting the acid halide corresponding to a carboxylic acid represented by the foregoing formula (III), preferably an acid chloride, with an alcohol represented by the foregoing formula (II) at from −30° to 100° C. for from 30 minutes to 20 hours in an inert solvent and in the presence of an acid-binding agent. The inert solvent includes for example benzene, toluene, hexane, diethyl ether, etc., and the acid-binding agent includes for example pyridine, triethylamine, etc. Referring to the amounts of the reagents used in this reaction, the carboxylic acid halide is used in an amount of usually from 0.9 to 1.5 equivalents, preferably from 0.95 to 1.1 equivalents based on 1 equivalent of the alcohol represented by the formula (II), and the acid-binding agent is used in an amount of usually from 1.0 to 2.0 equivalents, preferably from 1.0 to 1.2 equivalents based on the same. After completion of the reaction, usual after-treatment is applied, and if necessary, it suffices to apply purification by chromatography, etc.

For insects against which the present compounds are particularly efficacious, there are given the following:

Hemiptera: Planthoppers (Delphacidae) such as smaller brown planthopper (*Laodelphax striatellus*), brown planthopper (*Nilaparvata lugens*) and whitebacked rice planthopper (*Sogatella furcifera*); leafhoppers (Deltocephalidae) such as green rice leafhoppers (*Nephotettix cincticeps, Nephotettix nigropictus* and *Nephotettix virescens*); aphids (Aphididae); bugs; whiteflies (Aleyrodidae); scales; lace bugs (Tingidae); and psyllids (Psyllidae); etc.

Lepidoptera Pyralidae such as rice stem borer (*Chilo suppressalis*), rice leafroller (*Cnaphalocrocis medinalis*) and Indian meal moth (*Plodia interpunctella*); Noctuidae such as tobacco cutworm (*Spodoptera litura*), rice armyworm (*Pseudaletia separata*), cabbage armyworm (*Mamestra brassicae*), turnip cutworm (*Agrotis segetum*), black cutworm (*Agrotis ipsilon*) and *Heliothis* spp.; Pieridae such as common cabbageworm (*Pieris rapae crucivora*); Tortricidae such as *Adoxophyes* spp. and *Grapholita* spp.; Carposinidae; Lyonetiidae; Lymantriidae; Yponomautidae such as diamondback moth (*Plutella xylostella*); Tineidae such as casemaking clothes moth (*Tinea pellionella*) and webbing clothes moth (*Tineola bisselliella*); etc.

Diptera: *Culex* spp. such as common mosquito (*Culex pipiens pallens*) and *Culex tritaeniorhynchus; Aedes* spp. such as *Aedes aegypti, Aedes albopictus* and *Aedes togoi; Anopheles* spp. such as *Anopheles sinensis* and *Anopheles stephensi*; Chironomidae; Muscidae such as housefly (*Musca domestica*), little housefly (*Fannia canicularis*) and false stablefly (*Muscina stabulans*); Calliphoridae; Sarcophagidae; Anthomyiidae such as seedcorn maggot (*Delia platura*) and onion maggot (*Delia antiqua*); Tephritidae; Drosophilidae; Psychodidae; black flies (Simuliidae); Tabanidae and stable flies (Stomoxyidae); etc.

Coleoptera: Scarabaeidae such as cupreous chafer (*Anomala cuprea*) and soybean beetle (*Anomala rufocuprea*); weevils (Curculionidae) such as maize weevil (*Sitophilus zeamais*) and ricewater weevil (*Lissorhoptrus oryzophilus*); Tenebrionidae such as yellow mealworm (*Tenebrio molitor*) and red flour beetle (*Tribolium castaneum*); Chrysomelidae such as western corn rootworm (*Diabrotica virgifera*), southern corn rootworm (*Diabrotica undecimpunctaca howardi*), striped flea beetle (*Phyllotreta striolata*) and cucurbit leaf beetle (*Aulacophora femoralis*); Anobiidae; ladybirds (*Coccinellidae*) such as twenty-eight-spotted ladybird (*Henosepilachna vigintioctopunctata*); powder post beetles (Lyctidae); false powderpost beetles (Bostrychidae); Cerambycidae; Staphylinidae such as robe beetle (*Paederus fuscipes*); and Dermastidae such as varied carpet beetle (*Anthrenus verbasci*); etc.

Dictyoptera: Blattelidae such as German cockroach (*Blattella germanica*); and Blattidae such as smoky-brown cockroach (*Periplaneta fuliginosa*), American cockroach (*Periplaneta americana*), brown cockroach (*Periplaneta brunnea*) and oriental cockroach (*Blatta orientalis*); etc.

Thysanoptera: *Thrips palmi* and flower thrips (*Thrips hawaiiensis*); etc.

Hymenoptera: ants (Formicidae); hornests (Vespidae); bethylid wasps (Bethylidae); and sawflies (Tenthredinidae) such as cabbage sawfly (*Athalia rosae ruficornis*); etc.

Orthoptera: mole crickets (Gryllotalpidae); and grasshoppers (Acrididae); etc.

Siphonaptera: Pulicidae such as *Pulex irritans*; etc.

Anoplura: Pediculidae such as *Pediculus humanus capitis*; and *Pthirus pubis*; etc.

Isoptera: *Reticulitermes speratus*; and *Coptotermes formosanus*; etc

The present compounds exhibit a particularly excellent insecticidal effect against the foregoing insect pests in the forms of a fumigant, smoking formulation, oil spray, aerosol, etc.

When the present compounds are used as an active ingredient for insecticides, they may be used as they are without adding any other ingredients Usually, however, they are formulated into oil sprays, emulsifiable concentrates, wettable powders, flowable concentrates (e.g. water-based suspension formulations, water-based emulsion formulations), granules, dusts, aerosols, heating fumigants (e.g. mosquito coils, electric mosquito mats, electric non-mat formulation i.e. heating fumigation of such a form that a part of a porous absorptive wick is dipped in an insecticidal solution to allow it to absorb the solution and said wick is indirectly heated at the top to fumigate the absorbed insecticidal solution), heating smoking formulations (e.g. self-burning-type smoking formulations, chemical reaction-type smoking formulations, porous ceramic plate-type smoking formulations), foggings, ULV formulations, poisonous baits, etc. by mixing with solid carriers, liquid carriers, gaseous carriers, baits, etc. or impregnating into base materials (e.g. mosquito coil carriers, mats) and if necessary, by additionally adding surface active agents and other auxiliaries for formulation.

These preparations contain the present compounds as an active ingredient in an amount of, usually, from 0.001 to 95% by weight.

The solid carriers used in the formulation include for example fine powders or granules of clays (e.g. kaolin clay, diatomaceous earth, synthetic hydrated silicon dioxide, bentonite, Fubasami clay, terra alba), talcs, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. The liquid carriers include for example water, alcohols (e.g. methanol, ethanol), ketones (e.g. acetone, methyl ethyl ketone, cyclohexanone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethyl sulfoxide, vegetable oils (e.g. soybean oil, cotton seed oil), etc. The gaseous carriers, i.e. a propellant, include for example freon gas, butane gas, LPG (liquefied petroleum gas), dimethyl ether, carbon dioxide gas, etc.

The surface active agents include for example alkyl sulfates, alkylsulfonates, alkylarylsulfonates, alkyl aryl ethers and their polyoxyethylenized products, polyethylene glycol ethers, polyhydric alcohol esters, sugar alcohol derivatives, etc.

The auxiliaries for formulation such as fixing agents, dispersing agents, etc. include for example casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids), etc. The stabilizing agents include for example PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, etc.

The base material for mosquito coils includes for example mixtures of a vegetable powder (e.g. wood powder, Pyrethrum marc) with a binder (e.g. Tabu powder, starch, gluten).

The base material for electric mosquito mats includes for example plate-like pressed products of fibrils of cotton linters or a mixture of cotton linters and pulp.

The base material for self-burning-type smoking formulations includes for example burning.heat-generating agents such as nitrates, nitrites, guanidine salts, potassium chlorate, nitrocellulose, ethyl cellulose, wood powders, etc.; pyrolysis-promoting agents such as alkali metal salts, alkaline earth metal salts, dichromates, chromates, etc.; oxygen-supplying agents such as potassium nitrate, etc.; burning-supporting agents such as melamine, wheat starch, etc.; extenders such as diatomaceous earth, etc.; and binders such as synthetic pastes, etc.

The base material for chemical reaction-type smoking formulations includes for example heat-generating agents such as the sulfides, polysulfides, hydrosulfides or salt hydrates of alkali metals, calcium oxide, etc.; catalyzing agents such as carbonaceous substances, iron carbide, activated clay, etc.; organic foaming agents such as azodicarbonamide, benzenesulfonyl hydrazide, dinitrosopentamethylenetetramine, polystyrene, polyurethane, etc.; fillers such as natural fiber pieces, synthetic fiber pieces, etc.

The base material for the poisonous baits includes for example bait components (e.g. grain powders, vegetable essential oils, saccharides, crystalline cellulose), antioxidants (e.g. dibutylhydroxytoluene, nordihydroguaiaretic acid), preservatives (e.g. dehydroacetic acid), attractants (e.g. cheese perfume, onion perfume, peanut oil), etc. Further, red pepper powders etc. also are included as an agent for preventing children from eating by mistake.

The flowable concentrates (water-based suspension formulations or water-based emulsion formulations) are generally obtained by finely dispersing 1 to 75% of the active ingredient compounds in water containing 0.5 to 15% of a dispersing agent, 0.1 to 10% of a suspension auxiliary (e.g. protective colloids, compounds giving a thixotropic property) and 0 to 10% of a suitable auxiliary (e.g. defoaming agents, anticorrosives, stabilizing agents, spreading agents, penetration auxiliaries, antifreezing agents, antibacterial agents, antimolding agents). It is also possible to obtain oil-based suspension formulations by replacing water by an oil in which the active ingredient compounds are almost insoluble. The protective colloids include for example gelatin, casein, gums, cellulose ethers, polyvinyl alcohol, etc., and the compounds giving a thixotropic property include for example bentonite, aluminum magnesium silicate, xanthane gum, polyacrylic acid, etc.

The preparations thus obtained are used as they are or diluted with water, etc. Further, they may be used mixed with other insecticides, acaricides, nematocides, soil-pest controlling agents, fungicides, herbicides, plant growth regulators, synergists, fertilizers, soil improvers, etc., or may be used simultaneously with these chemicals without mixing.

When the present compounds are used as an active ingredient for agricultural insecticides, their dosage rate is usually from 5 to 500 g/10 ares. When the emulsifiable concentrates, wettable powders, flowable concentrates, etc. are used diluted with water, the application concentration of the active ingredient is from 0.1 to 1000 ppm. The granules, dusts, etc. are used as they are without being diluted. When the present compounds are used as an active ingredient for household and public hygienic insecticides, the emulsifiable concentrates, wettable powders, flowable concentrates, etc. are applied diluted with water to 0.1 to 10000 ppm, and the oil sprays, aerosols, fumigants, smoking formulations, foggings, ULV formulations, poisonous baits, etc. are applied as they are.

Although any of these dosage rate and application concentration varies with the kind of preparations, when, where and how these preparations are applied, the kind of insect pests, the degree of damage, etc., they may be increased or decreased independently of the ranges explained above.

The present invention will be illustrated in more detail with reference to the following production examples, formulation examples and test examples, but it is not limited to these examples.

First, production examples for the present compounds will be shown.

Production Example 1

Production of the Present Compound (1)

317 Milligrams of (S)-2-methyl-3-propargyl-4-oxo-2-cyclopenten-1-ol and 500 mg of (1R, trans, E)-2,2-dimethyl-3-(2-fluoro-2-ethoxycarbonylvinyl)cyclopropanecarboxylic acid chloride were dissolved in 5 ml of dry toluene, and 220 mg of pyridine was added dropwise thereto with ice-cooling. After the reaction solution was stirred overnight at room temperature, it was poured into a 5% hydrochloric acid and extracted with ethyl acetate. The ethyl acetate layer was successively washed with a saturated aqueous sodium hydrogencarbonate solution, water and a saturated aqueous sodium chloride solution and dried over anhydrous magnesium sulfate. The solvent was removed under reduced pressure, and the residue obtained was treated by chromatography on silica gel (developing solvent, hexane:ethyl acetate=3:1) to obtain 540 mg of the desired compound as a pale yellow oily product. The yield based on the carboxylic acid chloride was 74.6%.

$n^{23}_D$ 1.5087.

$^1$H-NMR (solvent, CDCl$_3$; δ value): 1.20–1.38 (m, 9H), 2.18 (s, 3H), 1.48–3.0 (m, 5H), 3.19 (d, 2H), 4.0–4.50 (m, 2H), 5.7 (bd, 1H), 5.71 (dd, 1H, J=10.8 Hz, 19.8 Hz).

Production Example 2

Production of the Present Compound (3)

226 Milligrams of (S)-2-methyl-3-propargyl-4-oxo-2-cyclopenten-1-ol and 420 mg of (1R, trans, Z)-2,2-dimethyl-3-(2-fluoro-2-ethoxycarbonylvinyl)cyclopropanecarboxylic acid chloride were dissolved in 5 ml of dry toluene, and 180 mg of pyridine was added dropwise thereto with ice-cooling. After the reaction solution was stirred overnight at room temperature, it was treated in the same manner as in Production example 1 to obtain 390 mg of the desired compound as a pale yellow oily product. The yield based on the carboxylic acid chloride was 63.7%.

$n^{21}_D$ 1.5136.

$^1$H-NMR (solvent, CDCl$_3$; δ value): 1.05–1.50 (m, 9H), 1.7–3.0 (m, 5H), 2.17 (s, 3H), 3.17 (d, 2H), 4.03–4.50 (m, 2H), 5.72 (bd, 1H), 5.85 (dd, 1H, J=10.8 Hz, 30.1 Hz).

Production Example 3

Production of the Present Compound (4)

423 Milligrams of (S)-2-methyl-3-propargyl-4-oxo-2-cyclopenten-1-ol and 650 mg of (1R, cis, E)-2,2-dimethyl-3-(2-fluoro-2-ethoxycarbonylvinyl)cyclopropanecarboxylic acid chloride were dissolved in 5 ml of dry toluene, and 290 mg of pyridine was added dropwise thereto with ice-cooling. After the reaction solution was stirred overnight at room temperature, it was treated in the same manner as in Production example 1 to obtain 680 mg of the desired compound as a pale yellow oily product. The yield based on the carboxylic acid chloride was 71.6%.

$n^{22}_D$ 1.5091.

$[\alpha]^{24}_D$ +34.9(CHCl$_3$).

$^1$H-NMR (solvent, CDCl$_3$; δ value): 1.3 (s, 6H), 1.38 (t, 3H), 2.17 (s, 3H), 1.90–3.0 (m, 5H), 3.17 (d, 2H), 4.0–4.55 (m, 2H), 5.5–6.0 (bd, 1H), 6.4 j(dd, 1H, J=10.8 Hz, 21.6 Hz).

Some of the present compounds produced according to the foregoing methods will be shown in Table 1.

TABLE 1

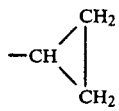

| Compound No. | R | Alcohol moiety | Acid moiety | Refractive index (°C.) |
|---|---|---|---|---|
| (1) | C$_2$H$_5$ | S | 1R, trans, E | 1.5087 (23) |
| (2) | CH$_3$ | S | 1R, cis, E | 1.5072 (23) |
| (3) | C$_2$H$_5$ | S | 1R, trans, Z | 1.5136 (21) |
| (4) | C$_2$H$_5$ | S | 1R, cis, E | 1.5091 (22) |
| (5) | C$_3$H$_7$-n | S | 1R, cis, E | 1.5079 (22) |
| (6) | C$_2$H$_5$ | RS | 1R, cis, E | 1.5085 (22) |
| (7) | —CH(CH$_2$)(CH$_2$) (cyclopropyl) | S | 1R, cis, E | 1.5090 (23) |
| (8) | —CH(CH$_2$)(CH$_2$) (cyclopropyl) | S | 1R, cis, E | 1.5073 (24) |
| (9) | C$_5$H$_{11}$-n | S | 1R, cis, E | 1.5098 (23) |
| (10) | CH$_2$CH=CH$_2$ | S | 1R, cis, E | 1.5091 (22) |
| (11) | CH$_2$C≡CH | S | 1R, cis, E | 1.5045 (22) |
| (12) | C$_3$H$_7$-i | S | 1R, cis, E | 1.5082 (24) |
| (13) | CH$_2$CH$_2$F | S | 1R, cis, E | 1.5005 (20) |
| (14) | CH$_2$Cl | S | 1R, cis, E | 1.5160 (21) |
| (15) | CH$_2$CH$_2$Cl | S | 1R, cis, E | 1.5152 (22) |
| (16) | C$_4$H$_9$-t | S | 1R, cis, E | 1.5077 (23) |
| (17) | C$_2$H$_5$ | S | 1R, cis, Z | 1.5142 (21) |

Formulation examples for insecticides containing the present compounds as an active ingredient will be shown. In the following examples, parts are by weight.

Formulation Example 1

Emulsifiable Concentrate

Ten parts of each of the present compounds (1) to (17) is dissolved in a mixture of 35 parts of xylene and 35 parts of dimethylformamide, and 14 parts of polyoxyethylene styrylphenyl ether and 6 parts of calcium dodecylbenzenesulfonate are added thereto. The resulting mixture is well stirred and mixed to obtain a 10% emulsifiable concentrate of each compound.

Formulation Example 2

Wettable Powder

Twenty parts of the present compound (1) is added to a mixture of 4 parts of sodium lauryl sulfate, 2 parts of calcium lignosulfonate, 20 parts of a fine powder of synthetic hydrated silicon dioxide and 54 parts of diatomaceous earth. The resulting mixture is stirred and mixed on a juice mixer to obtain a 20% wettable powder.

Formulation Example 3

Granule

To 5 parts of the present compound (2) are added 5 parts of sodium dodecylbenzenesulfonate, 30 parts of bentonite and 60 parts of clay, and the mixture is well stirred and mixed. A suitable amount of water is added to the mixture, and the mixture is further stirred, granulated on a granulator and air-dried to obtain a 5% granule.

Formulation Example 4

Dust

One part of the present compound (3) is dissolved in a suitable amount of acetone, and to the resulting solution are added 5 parts of a fine powder of synthetic hydrated silicon dioxide, 0.3 part of PAP and 93.7 parts of clay. The mixture is stirred and mixed on a juice mixer, and acetone is removed by vaporization to obtain a 1% dust.

Formulation Example 5

Flowable concentrate

Ten parts of the present compound (4) is added to 40 parts of an aqueous solution containing 6 parts of polyvinyl alcohol, and the resulting mixture is stirred on a mixer to obtain a dispersion. To this dispersion are added 40 parts of an aqueous solution containing 0.05 part of xanthane gum and 0.1 part of aluminum magnesium silicate and then 10 parts of propylene glycol. The mixture is mildly stirred and mixed to obtain a 10% water-based emulsion formulation.

Formulation Example 6

Oil spray 0.1 Part of each of the present compounds (1) to (17) is dissolved in a mixture of 5 parts of xylene and 5 parts of trichloroethane, and the resulting solution is mixed with 89.9 parts of kerosene to obtain a 0.1% oil spray of each compound.

Formulation Example 7

Oil-based aerosol 0.2 Part of the present compound (4), 0.1 part of d-Phenothrin, 10 parts of trichloroethane and 59.7 parts of kerosene are mixed to prepare a solution. The solution is filled in an aerosol container. After mounting a valve portion on the container, 30 parts of a propellant (liquefied petroleum gas) is charged into the container under pressure through the valve portion to obtain an oil-based aerosol.

Formulation Example 8

Water-Based Aerosol 0.3 Part of the present compound (5), 0.2 part of d-Phenothrin, 5 parts of xylene, 3.5 parts of kerosene and 1 part of an emulsifier (Atmos 300, a registered trademark of Atlas Chemical Co., Ltd.) are mixed to prepare a solution. The solution and 50 parts of pure water are filled in an aerosol container. After mounting a valve portion on the container, 40 parts of a propellant (liquefied petroleum gas) is charged into the container under pressure through the valve portion to obtain a water-based aerosol.

Formulation Example 9

Mosquito Coil 0.3 Gram of the present compound (6) is dissolved in 20 ml of acetone, and the resulting solution is uniformly mixed with 99.4 g of a mosquito coil carrier (a mixture of Tabu powder, Pyrethrum marc and wood powder in a ratio of 4:3:3) with stirring. Thereafter, 120 ml of water is added, and the mixture is well kneaded, shaped into a mosquito coil and dried. Thus, a mosquito coil is obtained.

Formulation Example 10

Electric mosquito Mat 0.4 Gram of the present compound (13) and 0.4 g of piperonyl butoxide are dissolved in acetone, and the total volume of the solution is made up to 10 ml with acetone. Thereafter, 0.5 ml of this solution is uniformly impregnated into a base material for electric mat, which is a plate-like pressed product of fibrils of a mixture of cotton linters and pulp, having a size of 2.5 cm x 1.5 cm x 0.3 cm (thick). Thus, an electric mosquito mat formulation is obtained.

Formulation Example 11

Heating Smoking Formulation

100 Milligrams of the present compound (14) is dissolved in a suitable amount of acetone and impregnated into a porous ceramic plate having a size of $4.0 \times 4.0$ cm $\times 1.2$ cm (thick) to obtain a heating smoking formulation.

Test examples on an insecticidal method using the present compounds will be shown below. The present compounds are shown by Compound Nos. in Table 1, and compounds used as a control are shown by compound symbols in Table 2.

TABLE 2

| Compound symbol | Structural formula | Alcohol moiety | Acid moiety | Remarks |
|---|---|---|---|---|
| (A) | $(CH_3O)_2PSCHCOOC_2H_5$ / $CH_2COOC_2H_5$ (S double bond on P) | — | — | Malathion |
| (B) | [structure with allyl cyclopentenone ester, F and COOC$_2$H$_5$ substituents] | S | 1R-cis-E | Compound disclosed in Example 42 of U.S. Pat. No. 4,489,093 |
| (C) | [structure with allyl cyclopentenone ester, F and COOCH$_3$ substituents] | S | 1R-cis-E | Compound disclosed in Example 49 of U.S. Pat. No. 4,489,093 |
| (D) | [structure with allyl cyclopentenone ester, COOC$_2$H$_5$ and F substituents] | S | 1R-cis-Z | Compound disclosed in Example 59 of U.S. Pat. No. 4,489,093 |
| (E) | [structure with propargyl cyclopentenone ester, CH$_3$ and COOC$_2$H$_5$ substituents] | S | 1R-cis-Z | Compound (25) disclosed in EP-A-0345801 |

TABLE 2-continued

| Compound symbol | Structural formula | Alcohol moiety | Acid moiety | Remarks |
| --- | --- | --- | --- | --- |
| (F) | [structure with CH₃, COOCH₃ groups] | S | 1R-cis-Z | Compound (2) disclosed in JP-B-52-45768 |
| (G) | [structure with COOC₂H₅, CH₃ groups] | S | 1R-cis-E | Compound (5) disclosed in EP-A-0345801 |
| (H) | [structure with CH₃, CH₃ groups] | S | 1R-cis | isomer of Compound (3) disclosed in U.S. Pat. No. 3,876,681 |
| (I) | [structure with CH₃, CH₃ groups] | S | 1R-cis | isomer of allethrin |

Test Example 1

The emulsifiable concentrates of the following present compounds obtained according to Formulation example 1 were each diluted 200 times with water (corresponding to 500 ppm), and 2 ml of the aqueous dilute solution was impregnated into 13 g of artificial diet for tobacco cutworm (*Spodoptera litura*). The artificial diet were put in a polyethylene cup of 11 cm in diameter, and then 10 fourth instar larvae of tobacco cutworm were liberated in the cup. After six days, the dead and alive of the larvae were examined to obtain a mortality. This test was repeated twice.

The results are shown in Table 3.

TABLE 3

| Test compound | Mortality (%) | Test compound | Mortality (%) |
| --- | --- | --- | --- |
| (1) | 100 | (10) | 100 |
| (2) | 100 | (11) | 100 |
| (3) | 100 | (12) | 100 |
| (4) | 100 | (13) | 100 |
| (5) | 100 | (14) | 100 |
| (6) | 100 | (15) | 100 |
| (7) | 100 | (16) | 100 |
| (8) | 100 | (17) | 100 |
| (9) | 100 | No treatment | 5 |

Test Example 2

The emulsifiable concentrates of the following present compounds and control obtained according to Formulation example 1 were each diluted 200 times with water (corresponding to 500 ppm), and rice seedlings (length, about 12 cm) were dipped for 1 minute in the aqueous dilute solution. After air-drying, the rice seedlings were put in a test tube, and 10 adults of resistant-strain green rice leafhopper (*Nephotettix cincticeps*) were liberated in the test tube. After one day, the dead and alive of the adults were examined to obtain a mortality. This test was repeated twice.

The results are shown in Table 4.

TABLE 4

| Test compound | Mortality (%) | Test compound | Mortality (%) |
| --- | --- | --- | --- |
| (1) | 100 | (11) | 100 |
| (2) | 100 | (12) | 100 |
| (3) | 100 | (13) | 100 |
| (4) | 100 | (14) | 100 |
| (5) | 100 | (15) | 100 |
| (6) | 100 | (16) | 100 |
| (7) | 100 | (17) | 100 |
| (8) | 100 | (A) | 50 |
| (9) | 100 | No treatment | 5 |
| (10) | 100 | | |

Test Example 3

Ten adults (male and female, 5 adults each) of German cockroach (*Blattella germanica*) were liberated in a polyethylene cup (diameter, 9 cm) coated thinly with vaseline at the inside wall. The cup was closed with a 16-mesh nylon gauze, and placed at the bottom of an acrylic cylinder of 10 cm in inside diameter and 37 cm in height. Thereafter, 0.6 ml of each of the 0.1% or 0.05% oil sprays of the present compounds and controls obtained according to Formulation example 6 was directly sprayed onto the insects by means of a spray gun at the top of the cylinder under a pressure of 0.6 atm. After 1.25 minutes elapsed, the number of the knocked-down insects was examined to obtain a percent knockdown. This test was repeated twice. The results are shown in Table 5.

Test Example 4

Housefly adults (*Musca domestica*) (female:male =1:1) were liberated in a 70 cm³ glass chamber (0.34

$m^3$). Thereafter, 0.7 ml of each of the 0.025% or 0.0125% oil sprays of the present compounds and controls obtained according to Formulation example 6 was sprayed by means of a spray gun under a pressure of 0.8 atm. After 2.5 minutes elapsed, the number of the knocked-down insects was examined to obtain a percent knock-down. This test was repeated twice. The results are shown in Table 5.

Test Example 5

Ten female adults of common mosquitoes (*Culex pipiens pallens*) were liberated in a (70 cm)3 glass chamber (0.34 m³). Thereafter, 0.7 ml of each of the 0.0125% or 0.00625% oil sprays of the present compounds and controls obtained according to Formulation example 6 was sprayed by means of a spray gun under a pressure of 0.8 atm. After the lapse of 24 minutes, the test insects were transferred to another vessel and given sugared water. After 24 hours, the dead and alive were counted for mortality. This test was repeated twice. The results are shown in Table 5.

TABLE 5

Test Results and Structural Characteristics of Present Compounds and Reference Ones.
(Corresponding to Test examples 3, 4 and 5)

[Structure: cyclopentenone with X substituent, bearing an ester linkage to a cyclopropane with Y group]

| Comp. | X— | Y | Alcohol moiety | Acid moiety | Test example 3 % Knock-down 0.1% | Test example 3 % Knock-down 0.05% | Test example 4 % Knock-down 0.025% | Test example 4 % Knock-down 0.0125% | Test example 5 % Mortality 0.0125% | Test example 5 % Mortality 0.00625% |
|---|---|---|---|---|---|---|---|---|---|---|
| (4) | CH≡CCH$_2$— | H, F (E), COOC$_2$H$_5$ | S | 1R-cis-E | 100 | 100 | 100 | 100 | 100 | 100 |
| (B) | CH$_2$=CHCH$_2$— | " | " | " | 45 | 0 | 15 | 0 | 30 | 10 |
| (E) | CH≡CCH$_2$— | H, CH$_3$ (Z), COOC$_2$H$_5$ | " | 1R-cis-Z | 100 | 15 | 100 | 10 | 60 | 30 |
| (2) | CH≡CCH$_2$— | H, F (E), COOCH$_3$ | S | 1R-cis-E | 100 | 100 | 100 | 100 | 100 | 100 |
| (C) | CH$_2$=CHCH$_2$— | " | " | " | 30 | 0 | 5 | 0 | 10 | 0 |
| (F) | CH≡CCH$_2$— | H, CH$_3$ (Z), COOCH$_3$ | " | 1R-cis-Z | 100 | 25 | 100 | 15 | 55 | 25 |
| (17) | CH≡CCH$_2$— | H, COOC$_2$H$_5$ (Z), F | S | 1R-cis-Z | 100 | 45 | 100 | 35 | 100 | 50 |
| (D) | CH$_2$=CHCH$_2$— | " | " | " | 5 | 0 | 0 | 0 | 0 | 0 |
| (G) | CH≡CCH$_2$— | H, COOC$_2$H$_5$ (E), CH$_3$ | " | 1R-cis-E | 20 | 0 | 10 | 0 | 5 | 0 |
| (H) | CH≡CCH$_2$— | H, CH$_3$, CH$_3$ | S | 1R-cis | 100 | 45 | 20 | 0 | 65 | 25 |
| (I) | CH$_2$=CHCH$_2$— | " | " | " | 75 | 15 | 10 | 0 | 40 | 15 |

What is claimed is:

1. A compound represented by the formula,

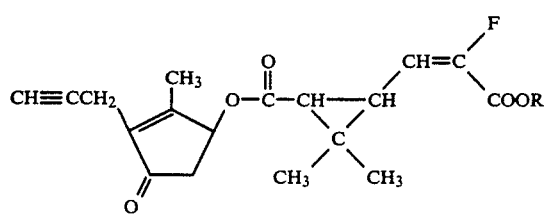

wherein R represents a C$_{1-5}$ alkyl group, a C$_{3-6}$ cycloalkyl group, a C$_{3-6}$ alkenyl group, a C$_{3-6}$ alkynyl group or a C$_{1-5}$ haloalkyl group.

2. A compound according to claim 1, wherein R represents a C$_{1-4}$ alkyl group, a cyclopropyl group, a $C_{3-4}$ alkenyl group, a $C_{3-4}$ alkynyl group or a $C_{1-4}$ haloalkyl group.

3. A compound according to claim 1, wherein R represents a methyl group, an ethyl group, a n-propyl group, an isopropyl group, a tert-butyl group, a cyclopropyl group, an allyl group, a propargyl group, a 2-chloroethyl group or a 2-fluoroethyl group.

4. A compound according to claim 1, wherein R represents a methyl group, an ethyl group, an isopropyl group or a tert-butyl group.

5. A compound of the formula,

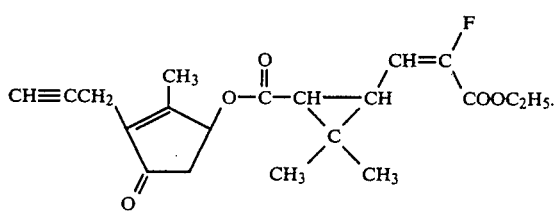

6. A compound of the formula,

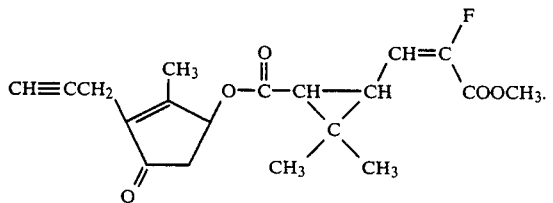

7. A compound of the formula,

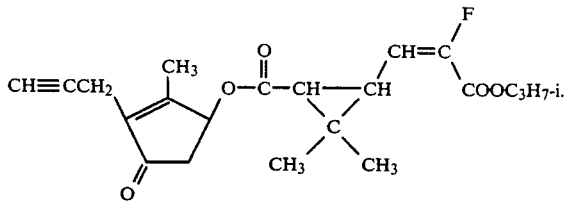

8. A compound of the formula,

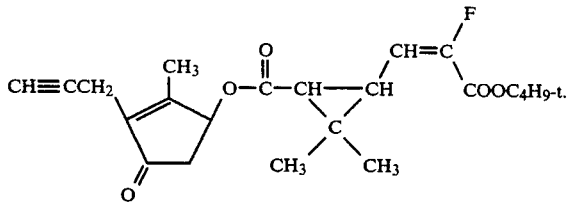

9. A compound of the formula,

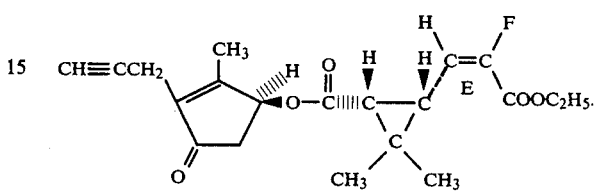

10. An insecticidal composition which comprises as an active ingredient an insecticidally effective amount of a compound represented by the formula,

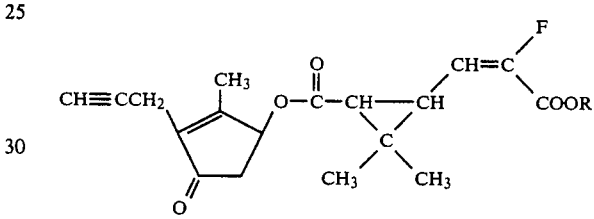

wherein R represents a $C_{1-5}$ alkyl group, a $C_{3-6}$ cycloalkyl group, a $C_{3-6}$ alkenyl group, a $C_{3-6}$ alkynyl group or a $C_{1-5}$ haloalkyl group, and an inert carrier.

11. An insecticidal composition according to claim 10, wherein R represents a $C_{1-4}$ alkyl group, a cyclopropyl group, a $C_{3-4}$ alkenyl group, a $C_{3-4}$ alkynyl group or a $C_{1-4}$ haloalkyl group.

12. An insecticidal composition according to claim 10, wherein R represents a methyl group, an ethyl group, a n-propyl group, an isopropyl group, a tert-butyl group, a cyclopropyl group, an allyl group, a propargyl group, a 2-chloroethyl group or a 2-fluoroethyl group.

13. An insecticidal composition according to claim 10, wherein R represents a methyl group, an ethyl group, an isopropyl group or a tert-butyl group.

14. A method for controlling insects which comprises applying an insecticidally effective amount of a compound according to claim 1 to the insects.

* * * * *